(12) United States Patent
Nakamura et al.

(10) Patent No.: US 9,107,576 B2
(45) Date of Patent: Aug. 18, 2015

(54) ENDOSCOPE INSERTION ASSISTING DEVICE

(75) Inventors: Takayuki Nakamura, Kanagawa (JP); Tsuyoshi Ashida, Kanagawa (JP); Yasunori Ohta, Kanagawa (JP); Shinichi Yamakawa, Kanagawa (JP); Rick Cornelius, Wayzata, MN (US); Charles Alan Brantingham, St. Paul, MN (US)

(73) Assignee: FUJIFILM Corporation, Tokyo (JP)

( * ) Notice: Subject to any disclaimer, the term of this patent is extended or adjusted under 35 U.S.C. 154(b) by 91 days.

(21) Appl. No.: 13/451,232

(22) Filed: Apr. 19, 2012

(65) Prior Publication Data

US 2012/0271105 A1 Oct. 25, 2012

Related U.S. Application Data

(60) Provisional application No. 61/477,376, filed on Apr. 20, 2011.

(51) Int. Cl.
| | |
|---|---|
| *A61B 1/00* | (2006.01) |
| *A61B 1/04* | (2006.01) |
| *A61M 31/00* | (2006.01) |
| *A61M 37/00* | (2006.01) |
| *G01N 21/00* | (2006.01) |
| *A61B 1/31* | (2006.01) |

(52) U.S. Cl.
CPC ........... *A61B 1/0016* (2013.01); *A61B 1/00101* (2013.01); *A61B 1/31* (2013.01)

(58) Field of Classification Search
USPC ......... 600/101, 104, 106, 107, 114–116, 127, 600/129; 604/95.01–95.05, 264, 271; 356/241.1–241.6
See application file for complete search history.

(56) References Cited

U.S. PATENT DOCUMENTS

| | | | |
|---|---|---|---|
| 2006/0089533 A1 | 4/2006 | Ziegler et al. | |
| 2008/0045790 A1* | 2/2008 | Ziegler et al. | 600/114 |
| 2010/0210900 A1* | 8/2010 | Allen et al. | 600/101 |

FOREIGN PATENT DOCUMENTS

JP 2009-513250 A 4/2009

* cited by examiner

*Primary Examiner* — Ryan Henderson
(74) *Attorney, Agent, or Firm* — Birch, Stewart, Kolasch & Birch, LLP

(57) ABSTRACT

An insertion assisting device includes a rotary body formed in a toroidal shape, and a support and drive unit that rotatably supports and rotates the rotary body. The support and drive unit has two supports, a first support and a second support. The first support is formed in a substantially cylindrical shape, and rotatably supports the rotary body. The second support is formed in a substantially triangular tubular shape, is arranged inside the first support, and supports driving gears that transmit a driving force to the rotary body. The second support is shorter than the first support, and is arranged so that front and rear end portions thereof are located inside front and rear end portions of the first support.

3 Claims, 7 Drawing Sheets

ENDOSCOPE INSERTION ASSISTING DEVICE

CROSS REFERENCE TO RELATED APPLICATIONS

This nonprovisional application claims the benefit of U.S. Provisional Application No. 61/477,376 filed on Apr. 20, 2011. The entire contents of the above application is hereby incorporated by reference.

BACKGROUND OF THE INVENTION

1. Field of the Invention

The present invention relates to an endoscope insertion assisting device having a rotary body formed in a toroid or belt shape that rotates to assist in insertion of an insertion part of an endoscope.

2. Description of the Related Art

In endoscopic examination, for example, insertion of an endoscope to the large intestine is very difficult because the large intestine has meandering structure in the body, an unfixed portion is present, or the like. For this reason, much experience is required for acquisition of the skill for insertion of the endoscope into the large intestine, and considerable pain will be inflicted on a subject when insertion skill is inexperienced.

The parts in the large intestine that are said to be particularly difficult to insert the endoscope into are the so-called sigmoid colon and the transverse colon. The reason is that, unlike other parts, the sigmoid colon and the transverse colon are not fixed within the body cavity, and thus, undergo arbitrary shape changes within a range of their own lengths or deform within the body cavity according to the contact force during insertion of the endoscope. For this reason, many techniques have been proposed that make it possible to make the sigmoid colon or the transverse colon straight so as to reduce contact of the endoscope with an intestinal tract during the insertion of the endoscope.

Additionally, an apparatus has also been proposed that self-propels an endoscope in an insertion direction within an intestinal tract so that insertion can be easily performed even if the insertion skill is inexperienced. For example, Japanese Patent Translation Publication No. 2009-513250 discloses an endoscope insertion assisting device having a rotary body formed in a toroidal shape (hollow cylindrical) that rotates to acquire a propulsive force in an insertion direction according to a frictional force generated between the outer surface of the rotary body and the intestinal wall.

In the insertion assisting device disclosed in the above Patent Document, the rotary body is pinched by driving gears arranged so as to have contact with the outer surface of the rotary body and driven rollers arranged so as to face the driving gears with the rotary body therebetween. The rotary body is rotated in accordance with the rotation of the driving gears.

Additionally, the insertion assisting device disclosed in the above Patent Document has two supports, a first support and a second support that are formed in a tubular shape. The first support is provided in a space inside the rotary body, thereby rotatably supporting the rotary body in a direction along the central axis thereof. Additionally, the first support rotatably supports the driven rollers in a state where the first support comes into contact with the inner surface of the rotary body that rotates inside the first support.

The second support is formed in a smaller diameter than the first support, and is held in a state where the second support is inserted through the first support. The second support rotatably supports the driving gears so that the driving gears come into contact with the outer surface of the rotary body that rotates inside of the first support, and holds a transmission mechanism that transmits a driving force to the driving gears. The rotary body is pinched between the driven rollers and the driving gears. Thereby, a driving force is transmitted to the rotary body supported by the respective supports via the transmission mechanism and the driving gears, and the rotary body rotates according to the rotation of the driving gears.

In the insertion assisting device disclosed in Japanese Translation Patent Publication No. 2009-513250, the second support is formed so as to be longer than the first support, and both ends of the second support protrude beyond both ends of the first support. If the ends of the second support protrude beyond the first support in this way, a clearance is formed between the rotary body and the second support at an end portion of the first support where the rotary body is turned.

For this reason, when the rotary body that rotates outside the first support is turned at the end of the first support, and enters between the first support and the second support, the inner wall of a body cavity brought into close contact with the rotary body due to mucus or the like and the inner wall of the body cavity collected on the rear side in a moving direction by the rotation of rotary body may be drawn-in between the respective supports. Such drawing-in of the inner wall of the body cavity will inflict pain on a subject or will cause a decline in propulsive force.

SUMMARY OF THE INVENTION

An object of the present invention is to provide an endoscope insertion assisting device capable of preventing an inner wall of a body cavity from being drawn-in between two tubular supports.

In order to achieve the above object, an endoscope insertion assisting device of the present invention includes a first support, a rotary body, a second support, a driving member, a pressing member, and an attachment member. The first support is formed in a substantially tubular shape. The rotary body is formed in a toroid or belt shape. The rotary body is wound around the first support so as to be rotatably supported, and is rotated so as to circulate inside and outside the first support. The second support is formed in a substantially tubular shape having a diameter smaller than that of the first support and is provided inside the first support. A second end portion of the second support is located inside a first end portion of the first support on a side where the rotary body is turned from outside to inside. The driving member is provided at one of the first support and the second support so as to come in contact with the rotary body. The driving member rotates in accordance with a driving force from a power source to transmit the driving force to the rotary body. The pressing member is provided at remaining one of the first support and the second support so as to face the driving member across the rotary body. The pressing member presses the rotary body against the driving member so as to appropriately transmit the driving force from the driving member to the rotary body. The attachment member detachably attaches the second support to an insertion part of an endoscope such that a rotational direction of the rotary body substantially coincides with an insertion direction of the insertion part.

Preferably, the second support is shorter than the first support, and is arranged such that both end portions thereof are located inside both end portions of the first support.

Preferably, an inward protruding portion that protrudes toward inside is provided at the first end portion of the first support. Preferably, the inward protruding portion protrudes slightly larger than an interval of a clearance formed between the first support and the second support. An outward protruding portion that protrudes toward outside may be provided at the first end portion of the first support.

Preferably, the endoscope insertion assisting device further includes a drawing-in preventing member provided at the second end portion of the second support so as to block the clearance formed between the first support and the second support. Preferably, the drawing-in preventing member is formed in a funnel shape whose diameter increases gradually, and a distal end of the drawing-in preventing member is brought into contact with the rotary body at a position inside the first end portion of the first support.

In the present invention, the end portion of the second support is located inside the end portion of the first support on a side where the rotary body is turned inward. Thereby, the clearance formed between the first support and the second support can be separated away from the end portion of the first support where the rotary body is turned. For this reason, there is a high possibility that the inner wall of a body cavity brought into close contact with the rotary body due to mucus or the like may be peeled from the rotary body while moving toward the clearance. Additionally, the inner wall of the body cavity collected on the rear side in a moving direction by the rotation of rotary body becomes difficult to enter the clearance. Accordingly, the inner wall of the body cavity can be prevented from being drawn-in between the respective supports.

BRIEF DESCRIPTION OF THE DRAWINGS

The above object and advantages can be easily understood by those skilled in the art by reading the detailed description of the preferred embodiments of the present invention with reference to the attached drawings.

DESCRIPTION OF THE PREFERRED EMBODIMENTS

Figure 1:
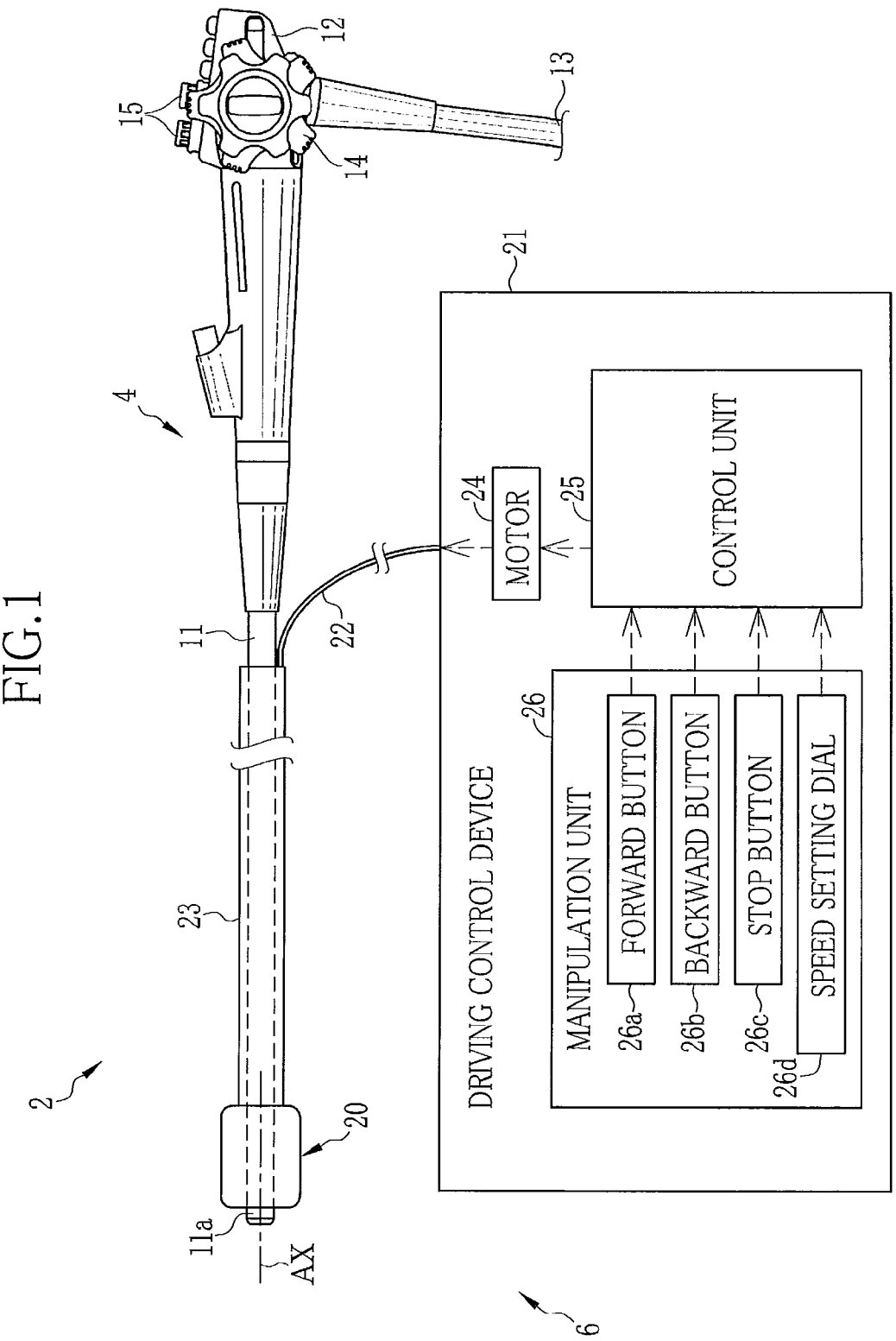
FIG. 1 is an explanatory view schematically showing the configuration of an endoscope system.

As shown in FIG. 1, an endoscope system 2 is constituted by an endoscope 4 for performing observation within the body cavity of a subject, and an insertion assisting unit 6 for assisting the insertion of the endoscope 4 into the body cavity. The endoscope 4 includes an insertion part 11 having a solid-state image sensing device (such as a CCD sensor, a CMOS sensor, or the like) built therein and adapted to be inserted into alimentary canals, such as the large intestine, a manipulating part 12 used for the grip of the endoscope 4 and the manipulation of the insertion part 11, and a universal cord 13 for connecting the endoscope 4 to a processor device or a light source device (none shown).

The insertion part 11 is a rod-shaped member having flexibility. A distal end portion 11a of the insertion part 11, as is well known, is provided with an observation window for taking in the image of an object, an illumination window for radiating illumination light, air and water supply nozzles for discharging air or water, or the like (none shown). The manipulating part 12 is equipped with an angle knob 14, manipulation buttons 15, and the like. The angle knob 14 is manipulated to rotate when the curving direction and curving amount of the insertion part 11 are adjusted. The manipulation buttons 15 are used for various kinds of manipulation, such as air supply, water supply, and suction.

The universal cord 13 is connected to the manipulating part 12. For example, a signal cable for outputting an imaging signal from the solid-state image sensing device to the processor device, a light guide for guiding the light emitted from the light source device to the distal end portion 11a, air and water supply channels that are conduits for sending air and water for air and water supply to the distal end portion 11a, and the like are incorporated into the universal cord 13.

The insertion assisting unit 6 is constituted by an insertion assisting device 20, a driving control device 21, a torque wire 22, and an overtube 23. The insertion assisting device 20 is detachably attached to the distal end portion 11a of the insertion part 11 and is provided to advance or retract the insertion part 11 within an alimentary canal. The driving control device 21 supplies a mechanical driving force to drive the insertion assisting device 20, and also performs control of the insertion assisting device 20, such as forward, backward or stop.

The torque wire 22 transmits a driving force from the driving control device 21 to the insertion assisting device 20. The torque wire 22 is covered with a protective sheath (not shown) over its total length. The torque wire 22 moves rotationally inside the protective sheath to transmit the driving force of the driving control device 21 to the insertion assisting device 20. Additionally, the torque wire 22 is detachably connected to the driving control device 21 via a well-known connector or the like.

The overtube 23 is externally fitted to the insertion part 11. The overtube 23 covers the insertion part 11 and the torque wire 22, and as the torque wire 22 is made to extend along the insertion part 11, the insertion part 11 and the torque wire 22 are put together. If so, the insertion part 11 and the torque wire 22 do not come apart within a body cavity, and handling of those can be facilitated. In addition, the overtube 23 is not limited to an overtube that covers the insertion part 11 from the distal end thereof to the vicinity of the proximal end thereof. For example, the overtube 23 may be a short overtube that covers only the vicinity of the distal end of the insertion part 11. Additionally, if the torque wire 22 does not get in the way, the overtube 23 is not necessarily provided.

The driving control device 21 is constituted by a motor 24 as a power source that generates a driving force for driving the insertion assisting device 20, a control unit 25 that controls the driving of the motor 24, and a manipulation unit 26 for inputting a manipulation instruction to the control unit 25. The motor 24 has a rotating shaft connected to the end of the torque wire 22 via a gear, a connector, or the like, and transmits the generated driving force to the torque wire 22. Thereby, the driving force of the motor 24 is transmitted to the insertion assisting device 20 via the torque wire 22.

The manipulation unit 26 is provided with a forward button 26a for instructing the advance of the insertion assisting device 20, a backward button 26b for instructing the retraction of the insertion assisting device 20, a stop button 26c for instructing the stop of the insertion assisting device 20, and a speed setting dial 26d for setting the moving speed of the insertion assisting device 20. The respective buttons 26a to 26c and the speed setting dial 26d are electrically connected to the control unit 25, and the result of a manipulation instruction therefrom is input to the control unit 25. The control unit 25 controls the rotation, stop, rotational direction or rotating speed of the motor 24 according to such an input from the manipulation unit 26.

Figure 2:
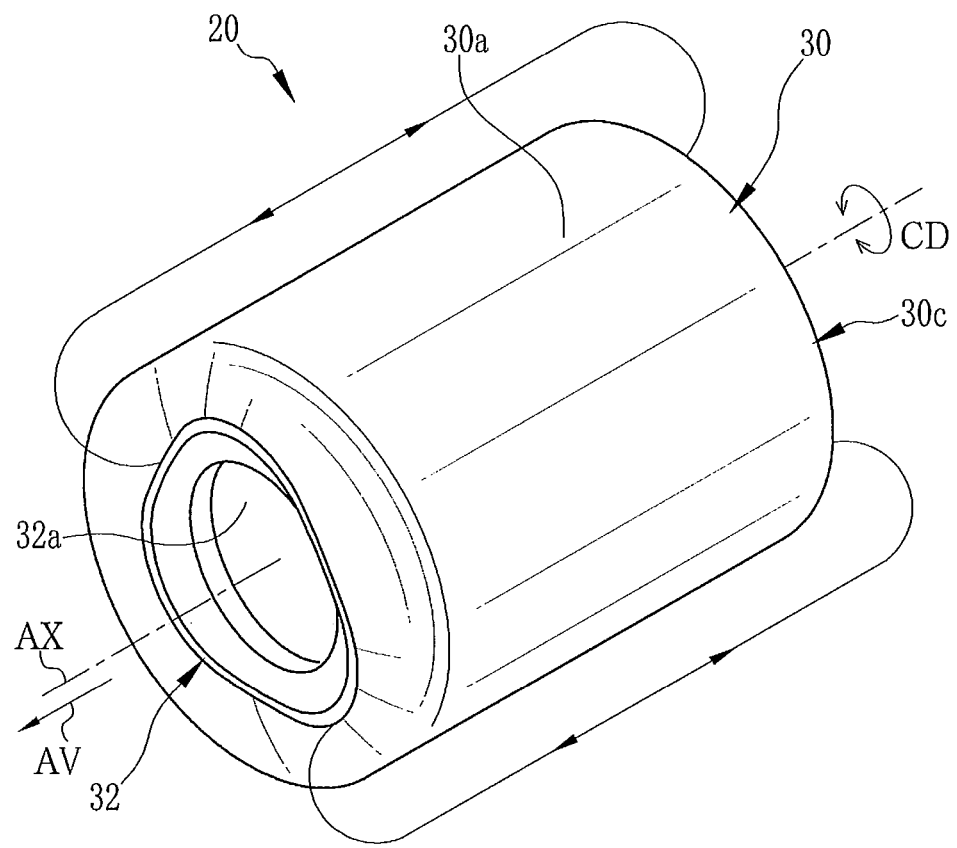
FIG. 2 is a perspective view showing the appearance of an insertion assisting device.

As shown in FIG. 2, the insertion assisting device 20 includes a rotary body 30 and a support and drive unit 32. The rotary body 30 is formed in a toroidal shape (a hollow cylindrical body) from a material having flexibility. The rotary body 30 rotates so that an outer surface 30a of the rotary body 30 is circulated in a direction along the central axis of the rotary body 30, and thereby generating a driving force for advancing or retracting the insertion part 11 within an alimentary canal. For example, flexible biocompatible plastics having flexibility, such as polyvinyl chloride, polyamide resin, fluororesin, and polyurethane, are used for the rotary body 30. The support and drive unit 32 rotatably supports the rotary body 30. The support and drive unit 32 transmits a driving force from the driving control device 21 transmitted via the torque wire 22 to rotate the rotary body 30.

The support and drive unit 32 is formed with an attachment member 32a for detachably attaching the insertion assisting device 20 to the insertion part 11 of the endoscope 4. The attachment member 32a is a substantially circular cross-sectional through hole formed in a direction along an insertion axis AX, and the diameter thereof is approximately equal to the diameter of the insertion part 11. Thereby, by fitting the insertion part 11 into the attachment member 32a, the insertion assisting device 20 is detachably attached to the insertion part 11 so that the rotational direction of the rotary body 30 and the insertion direction of the insertion part 11 of the endoscope 4 substantially coincide with each other.

The insertion assisting device 20 rotates the rotary body 30 in a state where the rotary body 30 is brought into contact with the inner wall of an alimentary canal, to advance or retract the insertion part 11, using a frictional force generated between the outer surface 30a of the rotary body 30 and the inner wall of the alimentary canal as a propulsive force. In a case where the insertion assisting device 20 is moved in an advancing direction shown by an arrow AV of FIG. 2 (namely, in the insertion direction), the outer surface 30a of the rotary body 30 in contact with the inner wall of the alimentary canal is moved in a retracting direction (namely, in a direction reverse to the direction shown by the arrow AV). The rotary body 30 moves in the retracting direction outside, and is then turned inward by 180° at its rear end portion. Then, the rotary body moves in the advancing direction inside, and is then turned outward again by 180° at its front end portion. In this way, the insertion assisting device 20 rotates the rotary body 30 so that the outside corresponds to the retracting direction and the inside corresponds to the advancing direction, thereby advancing the insertion part 11 of the endoscope 4. On the other hand, in a case where the insertion part 11 is moved in the retracting direction, the rotary body 30 is rotated in a direction reverse to the above.

Figure 3:
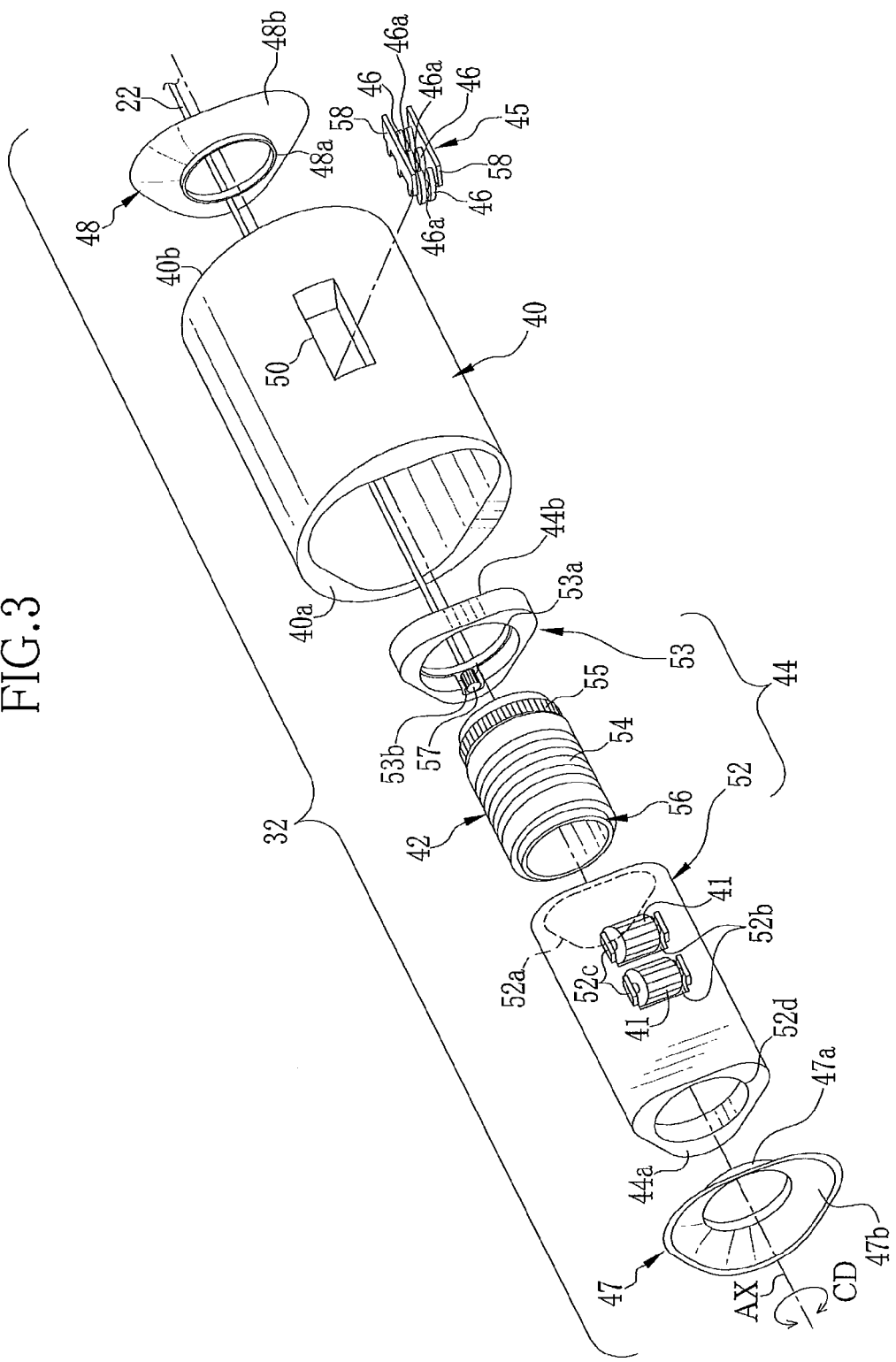
FIG. 3 is an exploded perspective view schematically showing the configuration of a support and drive unit.

As shown in FIG. 3, the support and drive unit 32 is constituted by a first support 40 that rotatably supports the rotary body 30, a plurality of driving gears 41 for rotating the rotary body 30, a gear barrel 42 that transmits a driving force to each of the driving gears 41, a second support 44 that turnably supports the respective driving gears 41 and the gear barrel 42, a roller unit 45 including a plurality of driven rollers 46 that presses the rotary body 30 against the driving gears 41, and first and second drawing-in preventing members 47 and 48 that prevent drawing-in of the inner wall of a body cavity into the support and drive unit 32.

The first support 40 has a tubular shape in which the cross-sectional shape thereof in a direction orthogonal to the insertion axis AX is circular at the outer peripheral surface and is substantially triangular (a shape in which respective apexes of an equilateral triangle are round) at the inner peripheral surface. The first support 40 is provided with three openings 50. The respective openings 50 are arranged at intervals of 120 degrees in a circumferential direction CD so as to be located on approximately flat portions of the inner peripheral surface of the first support 40. Additionally, each opening 50 is arranged near the center of the first support 40 in the insertion direction. Each of the openings 50 is used for the attachment of the roller unit 45.

Figure 4:
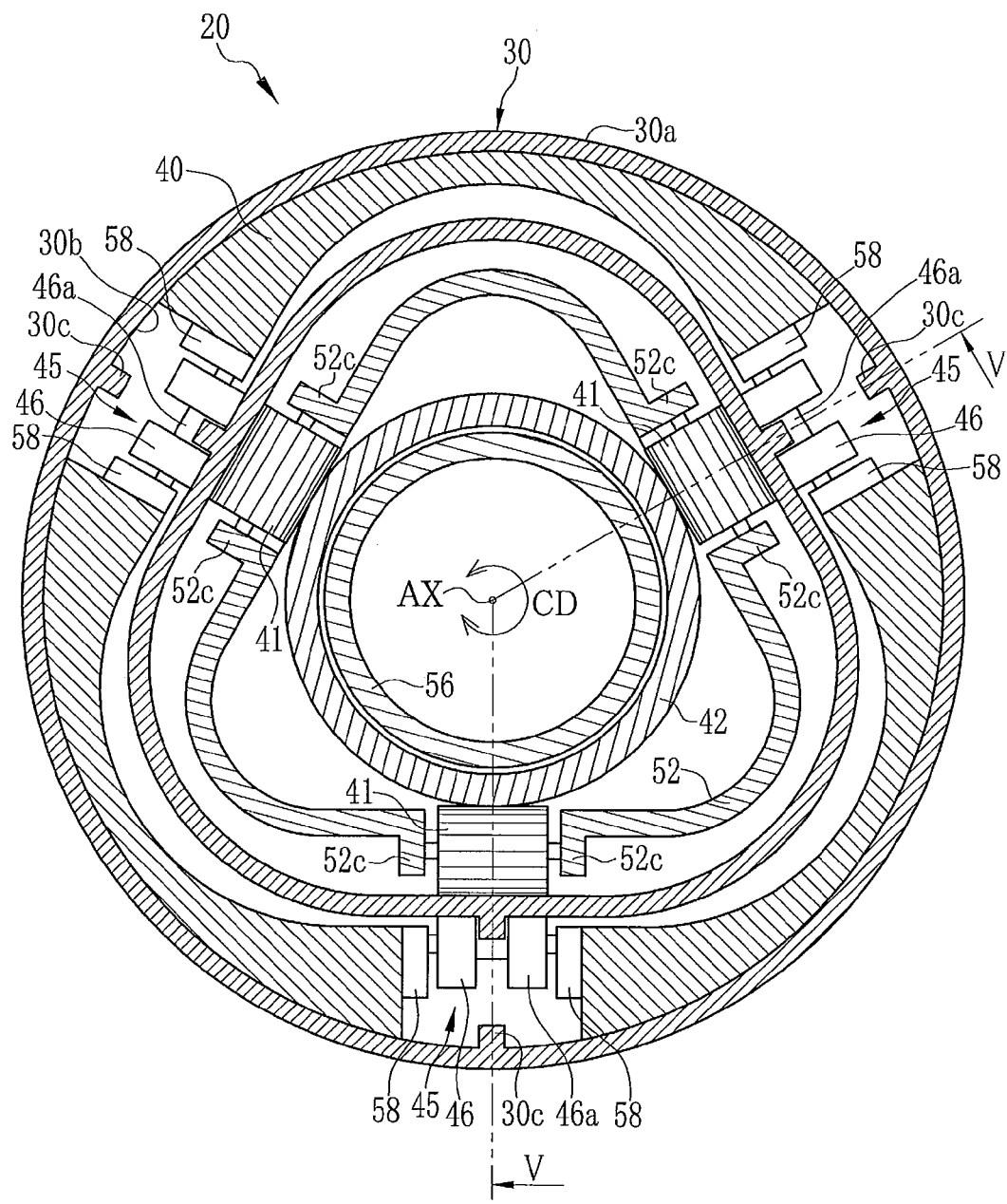
FIG. 4 is a cross-sectional view schematically showing the cross-sectional structure of the insertion assisting device in a direction orthogonal to an insertion direction.
Figure 5:
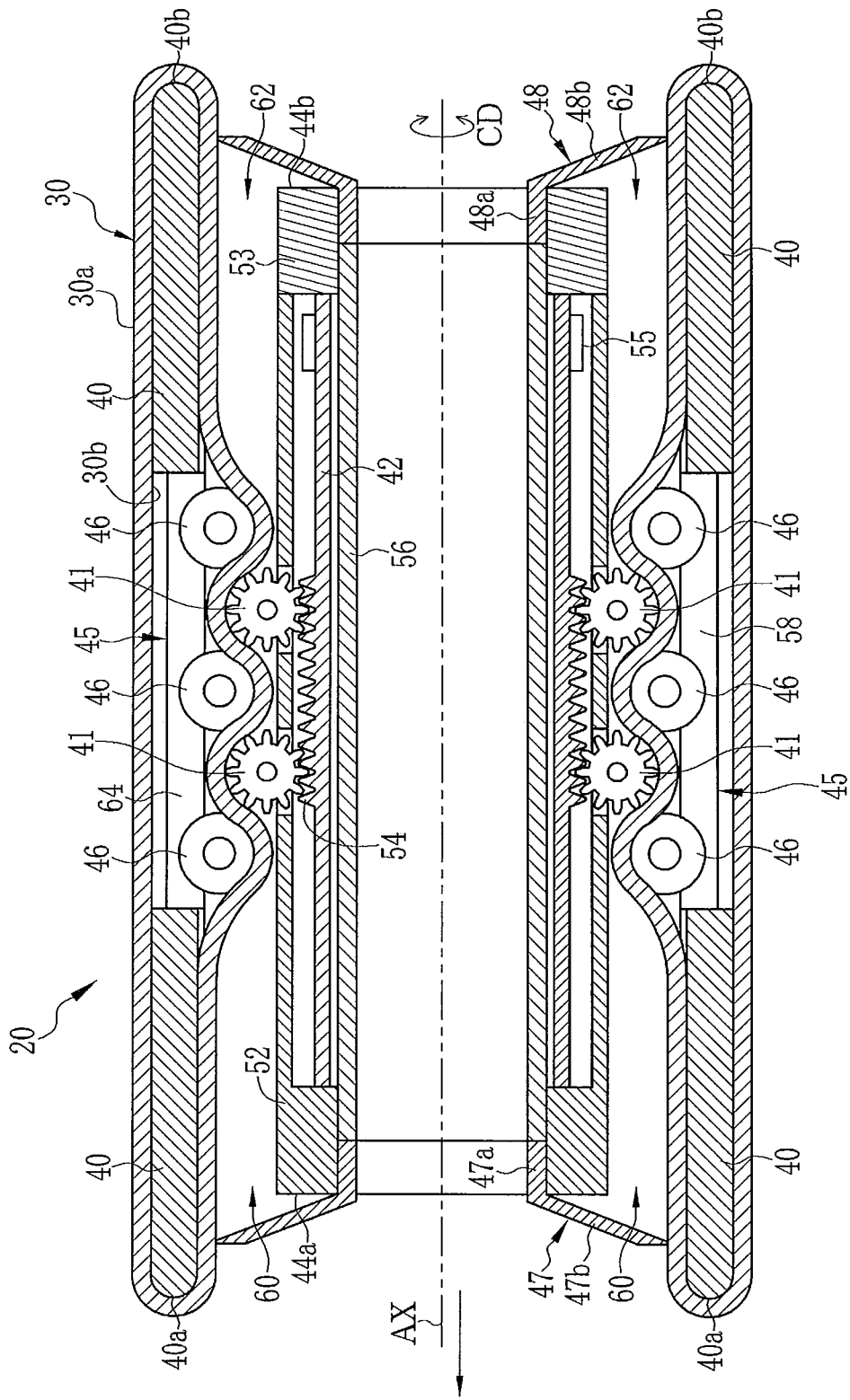
FIG. 5 is a cross-sectional view taken along lines V-V of FIG. 4.

As shown in FIGS. 4 and 5, the rotary body 30 is wound around the first support 40 so as to surround the overall first support 40. In this way, the first support 40 is located within the space surrounded by an inner surface 30b of the rotary body 30 formed in a toroidal shape, thereby rotatably supporting rotary body 30.

The rotary body 30 is made of a substantially rectangular sheet. When a 3-dimensional rotary body 30 is formed, first, both side ends of this sheet are bonded or welded together and are formed in a cylindrical shape, and the resulting cylinder is inserted through the inside of the first support 40. Then, the sheet formed in a cylindrical shape is folded back outward at a front end portion 40a and a rear end portion 40b of the first support 40, and both ends of the sheet are bonded or welded together. Thereby, a toroidal rotary body 30 is formed, and is wound around the first support 40 so as to surround the overall first support 40.

The respective driving gears 41, the gear barrel 42, and respective members of the second support 44 are incorporated into the space inside the first support 40 so as to be located inside the rotary body 30 that rotates inside the first support 40.

The second support 44 is constituted by a main body 52 that is formed in a triangular tubular shape having a cross-sectional shape slightly smaller than the inner peripheral surface of the first support 40, and a lid member (hereinafter abbreviated as lid) 53 fixed to the rear end of the main body 52. The lid 53 is fixed to an end portion at the opening 52a of the main body 52 by screwing or the like. Additionally, the second support 44 is shorter than the first support 40 in its length along the direction along the insertion axis AX.

The main body 52 has three flat lateral faces, and each of the lateral faces has two openings 52b formed in a substantially rectangular shape. The openings 52b are positioned so as to face the opening 50 formed in the lateral face of the first support 40 when the second support 44 is incorporated into the inside of the first support 40. Additionally, each lateral face of the main body 52 is formed with four struts 52c formed so as protrude substantially perpendicularly. Each strut 52c is arranged adjacent to the edge of each opening 52b, and extends in a direction substantially orthogonal to the insertion axis AX.

A total of six driving gears 41 are provided in twos on the respective lateral faces of the main body 52. Each driving gear 41 is arranged at a position corresponding to each opening 52b, and its rotating shaft is supported by each strut 52c, such that each driving gear 41 is rotatable around the direction substantially orthogonal to the insertion axis AX. As mentioned above, if the second support 44 is incorporated into the inside of the first support 40, the opening 50 of the first support 40 faces each opening 52b of the main body 52. Accordingly, if the second support 44 is incorporated into the inside of the first support 40, each driving gear 41 also faces the opening 50 of the first support 40.

The diameter of each driving gear 41 and the height of each strut 52c are adjusted, respectively so that a portion of the driving gear 41 enters the inside of the main body 52 via the opening 52b, and the driving gear 41 has contact with the outer surface 30a of the rotary body 30 that rotates inside the first support 40.

A worm 54 is formed on an outer surface of the gear barrel 42. Additionally, a spur gear 55 in which a plurality of teeth are arrayed in the circumferential direction is provided at the rear end portion of the gear barrel 42. In the state where the gear barrel 42 is supported by the second support 44, the diameter of and the teeth height of the worm 54 are adjusted, so that the worm 54 meshes with each driving gear 41 that has entered the inside of the main body 52. Accordingly, although the driving gear 41 is a worm wheel, the height of the teeth of the driving gear 41 is relatively low so as not to damage the rotary body 30.

The teeth of each driving gear 41 correspond to the inclination (pitch) of the spirally formed worm 54, and inclines slightly relative to the direction substantially orthogonal to the insertion axis AX. Thereby, if the gear barrel 42 rotates in the circumferential direction CD with the insertion axis AX as an axis, each driving gear 41 rotates around a direction substantially orthogonal to the insertion axis AX, in response to the engagement between the worm 54 and the driving gear 41.

A shaft barrel 56 formed in a substantially cylindrical shape is inserted through the gear barrel 42. The external diameter of the shaft barrel 56 is made almost equal to or slightly smaller than the internal diameter of the gear barrel 42. The internal diameter of the shaft barrel 56 is made almost equal to the diameter of the insertion part 11 of the endoscope 4. Thereby, the shaft barrel 56 turnably supports the gear barrel 42, and the inner surface thereof constitutes a portion of the attachment member 32a. Additionally, the shaft barrel 56 is formed so as to have a longer axial length than the gear barrel 42, and both ends thereof protrude from the gear barrel 42. The gear barrel 42 is turnably supported by the main body 52 and lid 53 of the second support 44 via both the protruding ends of the shaft barrel 56.

A pinion gear (pinion) 57 connected to the distal end of the torque wire 22 meshes with the spur gear 55 of the gear barrel 42. The pinion gear 57 is rotated by the torque wire 22, and transmits a driving force to the spur gear 55, thereby moving rotationally the gear barrel 42 along the outer periphery of the shaft barrel 56.

The rear end of the main body 52 has an opening 52a having an approximately triangular shape for introducing the gear barrel 42. The front end of the main body 52 has an opening 52d having an approximately circular shape into which one end of the shaft barrel 56 is fitted. A diameter of the opening 52d is substantially equal to the outer diameter of the shaft barrel 56. Accordingly, one end of the shaft barrel 56 is fitted into the opening 52d, and the gear barrel 42 is held in a rotatable manner by the main body 52.

The lid 53 has substantially the same shape as the front end portion of the main body 52 having the opening 52d, and fixed to the rear end of the main body 52. Further, the lid 53 has an approximately circular opening 53a into which the other end of the shaft barrel 56 is fitted. Accordingly, the gear barrel 42 is located between the main body 52 and the lid 53, and rotatable around the shaft barrel 56. The worm 54 enters in the internal space of the main body 52 and the spur gear 55 enters in the internal space of the lid 53.

The inner surface of the lid 53 has a recess 53b for housing the pinion gear 57. The recess 53b is formed such that the spur gear 55 entering in the internal space of the lid 53 meshes with the pinion gear 57 in a state that the gear barrel 42 is held in the rotatable manner between the main body 52 and the lid 53. The torque wire 22 is coupled to the pinion gear 57 through a through hole (not shown in the drawing) formed in a surface of the recess 53b orthogonal to the insertion axis AX.

The roller unit 45 is constituted by three driven rollers 46, and a pair of supporting plates 58 that turnably supports each of the driven rollers 46 from both sides. The roller unit 45 is inserted through the opening 50 from outside of the first support 40, and is attached to the first support 40 in a state where the respective driven rollers 46 have entered the inside of the first support 40. Thereby, the rotary body 30 is pinched by the respective driving gears 41 and the respective driven rollers 46. Further, each driven roller 46 faces each driving gear 41 with the rotary body 30 therebetween, and presses the rotary body 30 against each driving gear 41, such that a driving force accompanying the rotation of each driving gear 41 is appropriately transmitted to the rotary body 30.

If each driving gear 41 rotates with the rotation of the gear barrel 42, a driving force of each driving gear 41 is transmitted to the rotary body 30 by the pinching between each driving gear 41 and each driven roller 46 and the pressing against the driving gear 41, and thus the rotary body 30 is rotated.

Additionally, as shown in FIG. 5, the respective driving gears 41 and the respective driven rollers 46 are arranged at almost the same pitches, respectively, so that the respective driving gears 41 are located between the respective driven rollers 46, and arranged so as to shift by a ½ pitch in the direction along the insertion axis AX, in a state that the number of the driven rollers 46 is three and the number of the driving gears 41 is two. Moreover, the diameter and pitch of the respective driving gears 41 and respective driven roller 46 are adjusted so as to pinch the rotary body 30 in a partially overlapped state in the radial direction of the first support 40.

For this reason, the portion of the rotary body 30 pinched by each driving gear 41 and each driven roller 46 is curved in a wave shape. If the rotary body 30 is curved in this way, the contact area between each driving gear 41 or each driven roller 46 and the rotary body 30 becomes large compared to a case where the rotary body 30 in a linear state is pinched. Therefore, the driving force of each driving gear 41 can be more appropriately transmitted to the rotary body 30.

If the rotary body 30 is pinched as described above, the movement of the main body 52 in the direction along the insertion axis AX is regulated by each driving gear 41 and each driven roller 46 that overlap each other in the radial direction, and slip-out of respective members incorporated into the inside of the first support 40 from the first support 40 is prevented.

Each opening 52b formed in each lateral face of the main body 52 is positioned so as to face the opening 50 formed in the lateral face of the first support 40 when the second support 44 is incorporated into the inside of the first support 40, such that the center of the first support 40 substantially coincides with the center of the second support 44.

Accordingly, if each driving gear 41 and each driven roller 46 are made to mesh with each other and the second support 44 is made to support the first support 40 as described above, the second support 44 is arranged with respect to the first support 40 so that the positions of the centers of the respective supports 40 and 44 in the direction along the insertion axis AX substantially coincide with each other, a front end portion 44a of the second support 44 is located inside the front end portion 40a of the first support 40, and also a rear end portion 44b of the second support 44 is located inside the rear end portion 40b of the first support 40.

The inner surface 30b of the rotary body 30 is provided with substantially rectangular cross-sectional protruding portions 30c that protrudes in a streak shape along the rotational direction (refer to FIG. 4). Three protruding portions 30c are provided to each of the driven rollers 46, respectively, and are arranged at intervals of 120 degrees in the circumferential direction CD. A groove 46a that engages the protruding portion 30c is provided near the center of each driven roller 46. If the protruding portion 30c and the groove 46a are engaged with each other in this way, it is possible to prevent the rotary body 30 from rotating in the circumferential direction CD, prevent the insertion assisting device 20 from rotating in a spiral manner, or prevent the rotary body 30 from being twisted and abnormally rotating. In addition, it is preferable to apply lubricant between the protruding portion 30c and the groove 46a in order to enhance the slidability between both.

The first drawing-in preventing member 47 has a ring-shaped fitting portion 47a that fits into opening 52d of the main body 52, and a drawing-in preventing portion 47b formed in a funnel shape whose diameter increases gradually according to the distance away from the fitting portion 47a. A resin material having elasticity is used for the first drawing-in preventing member 47.

The external diameter of the fitting portion 47a is made almost equal to the diameter of opening 52d of the main body 52. Thereby, the fitting portion 47a fits into opening 52d, and the first drawing-in preventing member 47 is supported by the main body 52. The drawing-in preventing portion 47b is formed in almost the same triangular cross-sectional shape as the second support 44 or the like. Additionally, the shape of the end of the drawing-in preventing portion 47b is slightly larger than the shape of the inner surface of the first support 40.

Additionally, the axial length of the drawing-in preventing portion 47b is adjusted so that the distal end of the drawing-in preventing portion 47b is located inside the front end portion 40a of the first support 40 in a state where the first drawing-in preventing member 47 is held by the main body 52.

Thereby, the first drawing-in preventing member 47 brings the distal end of the drawing-in preventing portion 47b into slight contact with the outer surface 30a of the rotary body 30 that rotates inside the first support 40, elastically deforms the distal end, and blocks an opening 60 at the front end of an clearance formed between the first support 40 and the second support 44 with the drawing-in preventing portion 47b. The first drawing-in preventing member 47 blocks the opening 60 with the drawing-in preventing portion 47b in this way, thereby preventing the inner wall of a body cavity from being drawn-in into the clearance formed between the first support 40 and the second support 44. Additionally, since the drawing-in preventing portion 47b is formed in a funnel shape, the distal end of the drawing-in preventing portion 47b has contact with the outer surface 30a of the rotary body 30 at an acute angle. If such an acute contact is made, the inner wall of the body cavity that comes into close contact with the rotary body 30 can be easily peeled from the rotary body 30.

The second drawing-in preventing member 48, similarly to the first drawing-in preventing member 47, has a ring-shaped fitting portion 48a that fits into the opening 53a of the lid 53, and a drawing-in preventing portion 48b that has a funnel shape whose diameter increases gradually according to the distance from the fitting portion 48a, and blocks an opening 62 at the rear end of the clearance formed between the first support 40 and the second support 44. Since the configuration of second drawing-in preventing member 48 is the same as that of the first drawing-in preventing member 47, the detailed description thereof is omitted. Additionally, the second drawing-in preventing member 48 is provided with a through hole (not shown) for allowing the torque wire 22 to be inserted therethrough.

When the insertion assisting device 20 is assembled, first, the gear barrel 42 is housed inside the main body 52 of the second support 44 and the lid 53 is attached to the end of the main body 52 at the opening 52a, thereby turnably supporting the gear barrel 42 with the second support 44. Then, both side ends of the substantially rectangular sheet is bonded or welded together and formed in a cylindrical shape, and the sheet is put on the outside of the second support 44.

After the sheet is put on the second support 44 that supports the gear barrel 42, these are inserted through the inside of the first support 40. In this case, the cylindrical sheet is arranged by adjusting the longitudinal position thereof so that both ends thereof is exposed to the outside of the first support 40.

After the second support 44 and the sheet are inserted through the first support 40, the roller unit 45 is attached to a position corresponding to each opening 50, and the sheet is pinched by each driving gear 41 and each driven roller 46. Accordingly, slip-out of the second support 44 from the first support 40 is prevented by each driving gear 41 and each driven roller 46 that overlap each other in the radial direction. After the roller unit 45 is attached to make the first support 40 held by the second support 44, the sheet is folded back at the front end portion 40a and rear end portion 40b of the first support 40, and both ends of the sheet are bonded or welded together outside the first support 40, thereby forming the rotary body 30.

Then, the fitting portion 47a of the first drawing-in preventing member 47 is fitted into the opening 52d of the main body 52 so as to make the first drawing-in preventing member 47 held by the main body 52, and the fitting portion 48a of the second drawing-in preventing member 48 is fitted into the opening 53a of the lid 53 so as to make the second drawing-in preventing member 48 held by the lid 53. By assembling the respective portions in this way, the insertion assisting device 20 is constructed.

When the insertion assisting device 20 is constructed in this way, a continuous through hole is formed from the fitting portion 47a of the first drawing-in preventing member 47 through the opening 52d of the main body 52, the inner surface of the shaft barrel 56, and the opening 53a of the lid 53 to the fitting portion 48a of the second drawing-in preventing member 48, and this through hole is constructed as the attachment member 32a.

Next, an operation of the endoscope system 2 constructed as described above will be described. In a case where an operator such as a doctor or an engineer conducts examination within the body cavity of a subject with use of the endoscope system 2, first, the overtube 23 is inserted through the insertion part 11 of the endoscope 4 in a state where the torque wire 22 is passed through the overtube 23, and the overtube 23 is attached to the insertion part 11. Then, the distal end portion 11a of the insertion part 11 is fitted into the attachment member 32a of the support and drive unit 32, and the insertion assisting device 20 is attached to the distal end portion 11a.

After the insertion assisting device 20 and the overtube 23 are attached to the insertion part 11, the torque wire 22 is connected to the driving control device 21, and the universal cord 13 of the endoscope 4 is connected to the processor device or the light source device. Then, input of a power source to the processor device, the light source device, the driving control device 21, and the like is performed, thereby completing examination preparation. Then, the insertion part 11 of the endoscope 4 is inserted into the alimentary canal of a subject to start examination.

After the operator advances the distal end portion 11a to a predetermined position within the alimentary canal, for example, a position immediately before the sigmoid colon, the operator manipulates the forward button 26a provided at the manipulation unit 26 of the driving control device 21, and instructs advance of the insertion assisting device 20 to the control unit 25. If the advance is instructed, the control unit 25 drives the motor 24 and rotates the motor 24 in a direction according to advance at a speed in accordance with the instruction from the speed setting dial 26d.

If the motor 24 rotates, the driving force thereof is transmitted to the gear barrel 42 via the torque wire 22 and the pinion gear 57, and the gear barrel 42 rotates. If the gear barrel 42 rotates, each driving gear 41 rotates according to this. Then, if each driving gear 41 rotates, the driving force of each driving gear 41 is transmitted to the rotary body 30 by the pinching of the rotary body 30 between each driving gear 41 and each driven roller 46, and the rotary body 30 rotates. If the rotary body 30 rotates, the insertion assisting device 20 and the distal end portion 11a advances along the inner wall of a body cavity by the frictional force between the outer surface 30a and the inner wall of the body cavity.

In the insertion assisting device 20, the second support 44 is arranged so that the front end portion 44a of the second support 44 is located inside the front end portion 40a of the first support 40 and the rear end portion 44b of the second support 44 is located inside the rear end portion 40b of the first support 40. Thus, the openings 60 and 62 at the front and rear ends of the clearance formed between the first support 40 and the second support 44 can be separated from the front end portion 40a and the rear end portion 40b of the first support 40 where the rotary body 30 is turned.

If the rear end portion 40b of the first support 40 and the opening 62 of the clearance are separated away from each other when the rotary body 30 turned at the rear end portion 40b of the first support 40 enters between the respective supports 40 and 44, a possibility that the inner wall of the body cavity brought into close contact with the rotary body 30 due to with mucus or the like is peeled from the rotary body 30 becomes high. Additionally, the inner wall of the body cavity collected on the rear side in the moving direction, i.e., at the rear end of the insertion assisting device 20, by the rotation of the rotary body 30 becomes hard to enter the opening 62. Therefore, the inner wall of the body cavity can be prevented from being drawn-in between the respective supports 40 and 44.

Additionally, if the front end portion 44a of the second support 44 protrudes more than the front end portion 40a of the first support 40 as in the related art, the front end portion 44a of the second support 44 will come into contact with the inner wall of the body cavity earlier than the rotary body 30 turned at the front end portion 40a of the first support 40. Thus, there is a concern that a propulsive force may decline. In contrast, in the insertion assisting device 20, the front end portion 40a of the first support 40 protrudes more than the front end portion 44a of the second support 44. Thus, when contacting the inner wall of the body cavity, the rotary body 30 turned at the front end portion 40a of the first support 40 appropriately comes into contact with the inner wall of the body cavity. As a result, a decline in the propulsive force accompanying the contact of the front end portion 44a of the second support 44 can be prevented.

Additionally, in the insertion assisting device 20, respective drawing-in preventing members 47 and 48 block the openings 60 and 62. Thus, the inner wall of the body cavity can be more appropriately prevented from being drawn-in between the respective supports 40 and 44. In this case, since the distal ends of the respective drawing-in preventing portions 47b and 48b of the respective drawing-in preventing members 47 and 48 are located inside the front end portion 40a and the rear end portion 40b of the first support 40, there is not caused a decline in propulsive force due to the contact of the respective drawing-in preventing members 47 and 48 with the inner wall of the body cavity earlier than with the rotary body 30.

In a case where the operator identifies a part where a pathological change is suspected and wants to observe the part in more detail, the operator manipulates the stop button 26c of the manipulation unit 26 to instruct stop of the insertion assisting device 20 to the control unit 25. Upon receiving the instruction for stopping the insertion assisting device 20, the control unit 25 stops the driving of the motor 24, and stops the rotation of the rotary body 30.

Then, after the operator finishes observation up to a predetermined position, for example, the vicinity of a connection between the ascending colon and the cecum, the operator manipulates the backward button 26b of the manipulation unit 26 to instruct retraction of the insertion assisting device 20 to the control unit 25. Upon receiving the instruction for retracting the insertion assisting device 20, the control unit 25 rotates the motor 24 in a direction opposite to the advancing direction. Since the rotary body 30 is rotated in the opposite direction, the insertion assisting device 20 and the distal end portion 11a are retracted. The operator retracts the insertion assisting device 20 in this way, and pulls out the insertion part 11 from the body cavity of the subject, thereby terminating examination. Additionally, since the insertion assisting device 20 is formed in almost the same shape on the side of the front and rear ends, similarly to during the advance, the inner wall of the body cavity can be appropriately prevented from being drawn-in between the respective supports 40 and 44 during retraction.

Figure 6:
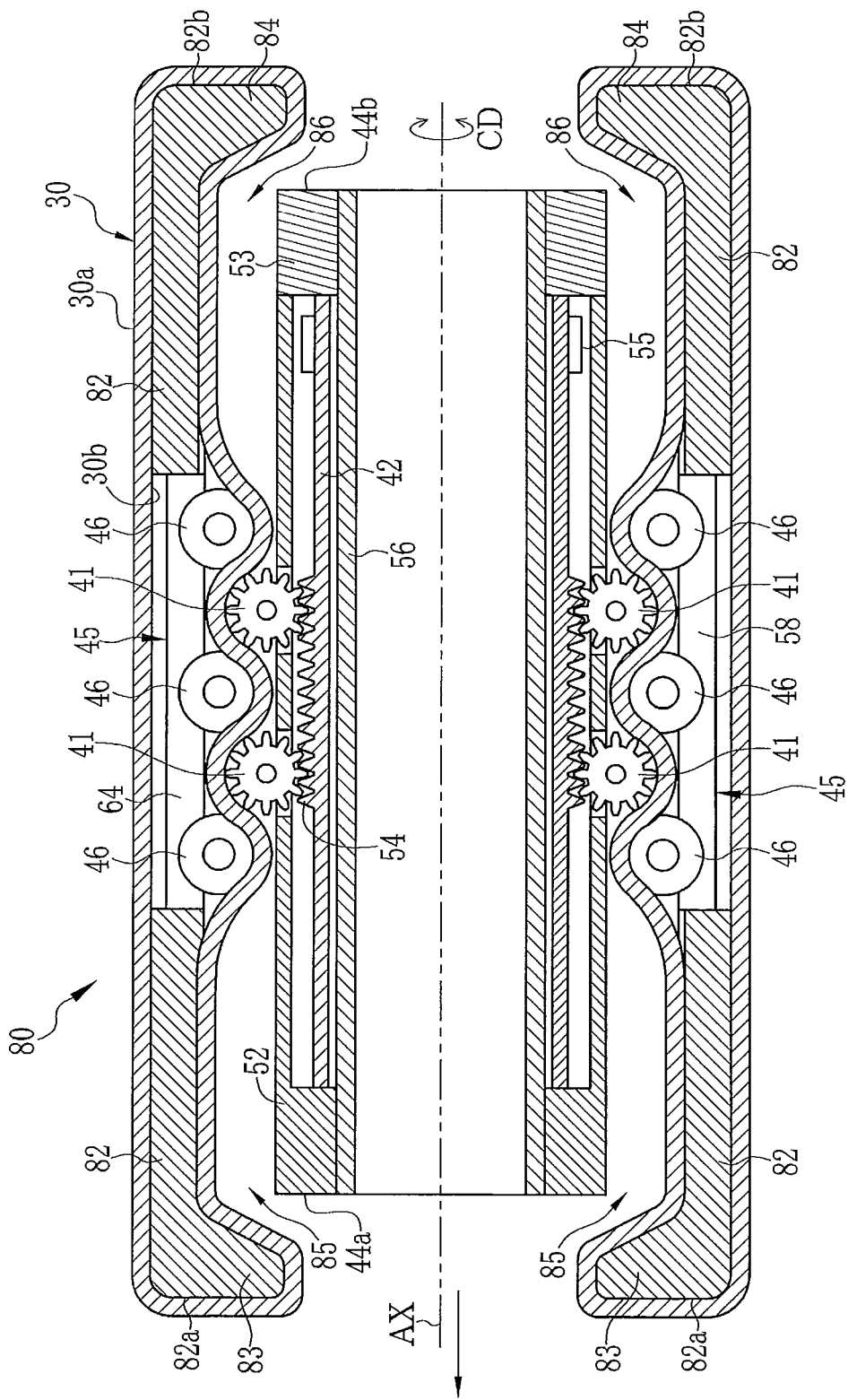
FIG. 6 is a cross-sectional view showing an example in which a first support is provided with a protruding portion that protrudes toward the inside.

Although the cylindrical first support 40 that is substantially uniform in thickness from the front end portion 40a to the rear end portion 40b is shown in the above embodiment, a first support 82 of an insertion assisting device 80 shown in FIG. 6 may be adopted. Note that, the same components as those of the above embodiment in terms of functions and configuration are designated by the same reference numerals, and the detailed description thereof is omitted.

In FIG. 6, protruding portions 83 and 84 that protrude toward the inside are provided at a front end portion 82a and a rear end portion 82b in the first support 82 of the insertion assisting device 80. The respective protruding portions 83 and 84 are formed with an amount of protrusion slightly larger than the clearance formed between the first support 82 and the second support 44. Thereby, the protruding portions 83 and 84 cover openings 85 and 86 at the front and rear ends of the clearance formed between the first support 82 and the second support 44, respectively, so that the openings 85 and 86 are not exposed in the direction along the insertion axis AX (namely, in a direction substantially orthogonal to the front end portion 82a and the rear end portion 82b).

If the openings 85 and 86 are covered with the protruding portions 83 and 84 provided at both end portions of the first support 82, the inner wall of a body cavity brought into close contact with the rotary body 30 due to mucus or the like is easily peeled from the rotary body 30. Further, the inner wall of the body cavity collected on the rear side in the moving direction becomes hard to enter the openings 85 and 86. Thus, the inner wall of the body cavity can be more appropriately prevented from being drawn-in between the respective supports 44 and 82.

In addition, although the amount of protrusion of each of the protruding portions 83 and 84 is made larger than the clearance formed between the respective supports 44 and 82 in the above first support 82, on the contrary to this, if the amount of protrusion of each of the protruding portions 83 and 84 is made smaller than the clearance formed between the respective supports 44 and 82, it is possible to prevent the drawing-in of the inner wall of the body cavity. Although it is believed that the drawing-in preventing effect is high in a case where the amount of protrusion is made larger than the clearance, if the amount of protrusion is made large too much, it is a concern that smooth rotation of the rotary body 30 may be hindered, or the propulsive force may be declined due to the contact with the insertion part 11. Accordingly, it is most preferable for the amount of protrusion of the respective protruding portions 83 and 84 to be set to be slightly larger than the clearance formed between the respective supports 44 and 82.

Additionally, if the first support 82 is integrally molded as one member when the respective protruding portions 83 and 84 are formed with an amount of protrusion larger than the clearance formed between the supports 44 and 82, the second support 44 or the like cannot be inserted through the inside of the first support 82. For this reason, in a case where the respective protruding portions 83 and 84 are formed with an amount of protrusion larger than the clearance formed between the supports 44 and 82, a portion including the protruding portion 83 or a portion including the protruding portion 84 of the first support 82 is made detachable, the second support 44 or the like is inserted through the inside of the first support 82 in a state where the portion described above is removed, and then the portion described above is attached to the first support 82, so as to construct the first support 82.

Although the respective drawing-in preventing members 47 and 48 are omitted, the insertion assisting device 80 may be provided with drawing-in preventing members that blocks the openings 85 and 86 similarly to the insertion assisting device 20 of the above embodiment.

Figure 7:
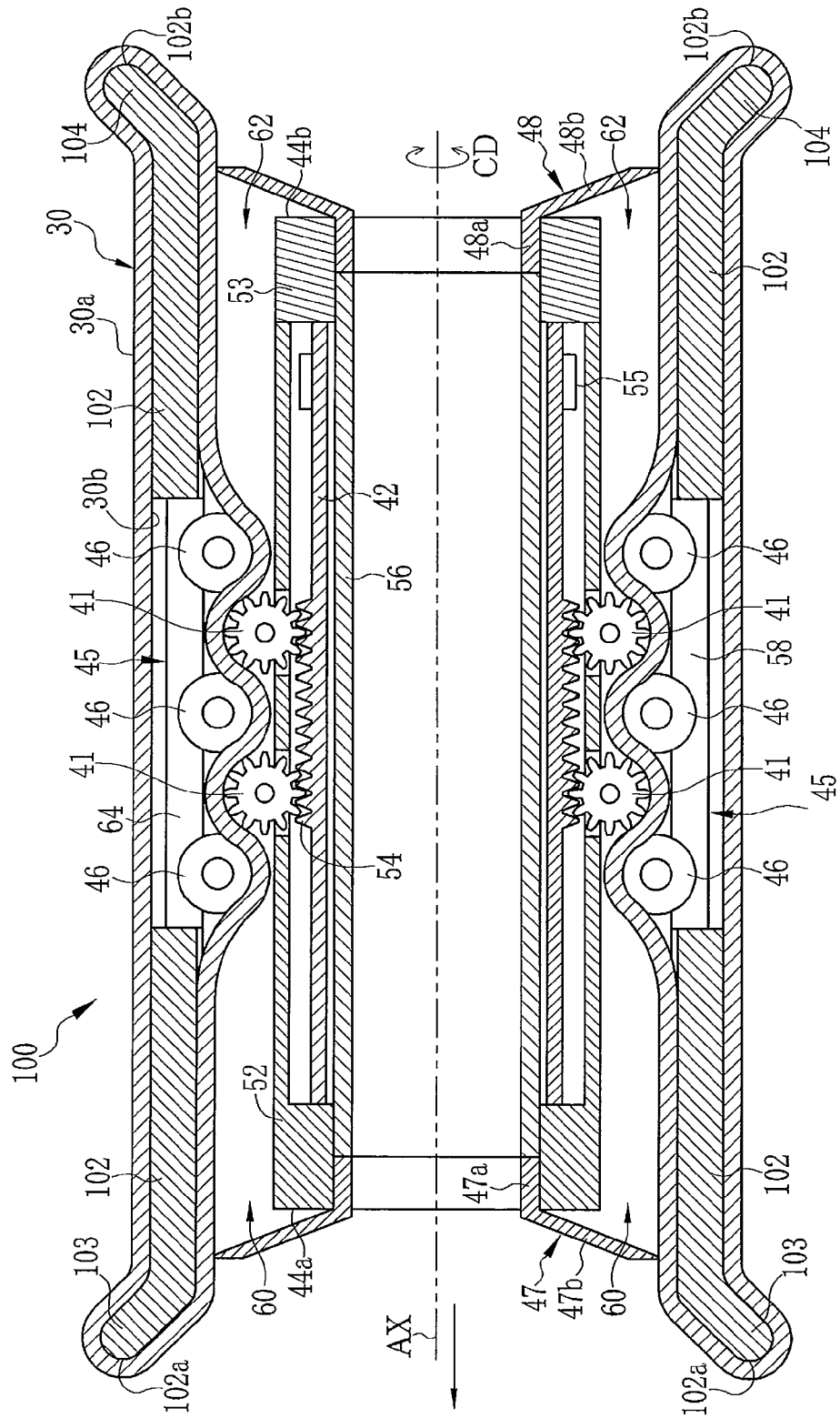
FIG. 7 is a cross-sectional view showing an example in which the first support is provided with a protruding portion that protrudes toward the outside.

In the insertion assisting device 80, the first support 82 having the protruding portions 83 and 84 that protrude toward the inside is shown. However, a first support 102 of an insertion assisting device 100 of FIG. 7, in which a front end portion 102*a* and a rear end portion 102*b* are provided with protruding portions 103 and 104 that protrude toward the outside, also may be adopted. The protruding portion 103 is formed in a bowl shape whose diameter becomes gradually large toward the front end. Similarly, the protruding portion 104 is formed in a bowl shape whose diameter becomes gradually large toward the rear end.

If the respective protruding portions 103 and 104 are formed in this way, the inner wall of a body cavity is pushed wide on the rear side in the moving direction. Thus, the inner wall of the body cavity brought into close contact with the rotary body 30 due to mucus or the like is easily peeled from the rotary body 30. As a result, the drawing-in preventing effect for the inner wall of the body cavity is high. In addition, the configuration of the first support 82 of FIG. 6 and the configuration of the first support 102 of FIG. 7 may be combined together so as to provide both the protruding portion that protrudes toward the inside and the protruding portion that protrudes toward the outside.

In the above embodiment, both the front end portion 44*a* and the rear end portion 44*b* of the second support 44 are adapted to be located inside the front end portion 40*a* and the rear end portion 40*b* of the first support 40. However, the present invention is not limited thereto.

For example, when the insertion assisting device 20 is used only during advance, only the rear end portion 44*b* of the second support 44 may be located inside the rear end portion 40*b* of the first support 40. Additionally, when the insertion assisting device 20 is used only during retraction, only the front end portion 44*a* of the second support 44 may be located inside the front end portion 40*a* of the first support 40. Either the front end portion 44*a* or the rear end portion 44*b* may be located inside in this way.

Additionally, in the above embodiment, the length of the second support 44 is made smaller than the length of the first support 40. However, in a case where one of the front end portion 44*a* and the rear end portion 44*b* is located inside, the length of the second support 44 is not necessarily made smaller than the length of the first support 40, and the remaining one of the front end portion 44*a* and the rear end portion 44*b* may be arranged so as to protrude.

Although the rotary body 30 is formed in a toroidal shape in the above embodiment, in addition to this, the shape of the rotary body 30 may be an endless belt or a belt with ends that is formed in a belt shape. In addition, in a case where the belt with ends is used, for example, as in the case of a magnetic tape of a cassette tape, a propulsive force for assisting in insertion of the insertion part 11 may be obtained by winding a belt around one rotating shaft in a roll shape, and making this belt move so as to be wrapped around the other rotating shaft.

In the above embodiment, the driving gears 41 that are worm wheels are used as driving members, and a driving force is transmitted to the rotary body 30 by the driving gears 41. However, the gear barrel 42 may be used as a driving member, and the rotary body 30 may be rotated by the worm 54. Additionally, the driving member may be a roller or the like. Further, although two driving gears 41 and three driven rollers 46 are used, one driving gear 41 and two driven rollers 46 may be used. Furthermore, three driving gears 41 and four driven rollers 46 may be used.

In the above embodiment, the driven rollers 46 are shown as pressing members. However, the pressing members may be plate-shaped or rod-shaped solid members having a smooth surface with little friction. Additionally, in a case where such solid members are used as the pressing members, it is preferable to press the pressing members against the rotary body 30 by elastic bodies such as springs.

In the above embodiment, a driving force is transmitted to the rotary body 30 at three positions. However, the present invention is not limited thereto, and a driving force may be transmitted at one position or two positions, or may be transmitted at four or more positions.

In the above embodiment, the cross-sectional shape of the second support 44 or the like is a substantially triangular shape. However, the cross-sectional shape of the second support 44 or the like may be other polygonal shapes such as circular, quadrangular, and hexagonal shapes, and may be suitably determined according to the position, number, or the like for transmitting a driving force. Additionally, although the substantially cylindrical first support 40 is shown in the above embodiment, the present invention is not limited thereto, and a tubular shape with a substantially polygonal cross-section may be adopted.

In the above embodiment, the driving control device 21 is provided with the motor 24 as a power source and the driving force of the motor 24 is transmitted to the insertion assisting device 20 via the torque wire 22. However, instead of this, power sources such as a motor may be provided inside the insertion assisting device 20. In this case, the number of power sources may be one, or plural. Additionally, the power source is not limited to the motor. For example, arbitrary power sources capable of generating a driving force such as an actuator may be used.

Additionally, in the above embodiment, the pressing members are arranged within the space inside the rotary body 30 and the driving members are arranged outside the rotary body 30. However, in a case where a power source is provided inside the insertion assisting device 20, in contrast, the driving members may be arranged within the space inside the rotary body 30, and the pressing members may be arranged outside the rotary body 30.

In the respective embodiments described above, the present invention is applied to an endoscope for medical diagnosis. However, the present invention is not limited to the application for medical diagnosis, and can also be applied to other endoscopes, probes, or the like for industrial use or the like.

What is claimed is:

1. An endoscope insertion assisting device comprising:
   a first support formed in a substantially tubular shape;
   a rotary body formed in a toroid or belt shape, said rotary body being wound around said first support so as to be rotatably supported, and being rotated so as to circulate inside and outside said first support;
   a second support formed in a substantially tubular shape having a diameter smaller than that of said first support and provided inside said first support;
   a driving member provided at one of said first support and said second support so as to come in contact with said rotary body, said driving member rotating in accordance with a driving force from a power source to transmit the driving force to said rotary body;
   a pressing member provided at remaining one of said first support and said second support so as to face said driving member across said rotary body, said pressing member pressing said rotary body against said driving member so as to appropriately transmit the driving force from said driving member to said rotary body; and
   an attachment member detachably attaching said second support to an insertion part of an endoscope so that a rotational direction of said rotary body substantially coincides with an insertion direction of said insertion part, and
   wherein each of the first support and second support have proximal and distal ends, and a distal end of the first support extends distally beyond a distal end of the second support, and a proximal end of the first support extends proximally beyond a proximal end of the second support, and
   the endoscope insertion assisting device further comprises:
   first and second drawing-in preventing members provided at the proximal and distal ends of said second support respectively, each of said drawing-in preventing members flaring radially outward and contacting said rotary body to prevent tissue from entering a gap formed between said first support and said second support,
   wherein the first drawing-in preventing member contacts the proximal end of the second support and a proximal end of the first drawing-in preventing member is positioned distal to the proximal end of the first support, and
   wherein the second drawing-in preventing member contacts the distal end of the second support and a distal end of the second drawing-in preventing member is positioned proximal to the distal end of the first support.

2. The endoscope insertion assisting device according to claim 1, wherein an outward protruding portion that protrudes toward outside is provided at said distal end of said first support.

3. The endoscope insertion assisting device according to claim 1, wherein one of said drawing-in preventing members is formed in a funnel shape whose diameter increases gradually, and a distal end of said drawing-in preventing member is brought into contact with said rotary body at a position proximal to said distal end of said first support.

\* \* \* \* \*